(12) United States Patent
Hedberg (10) Patent No.: US 8,556,792 B2
(45) Date of Patent: Oct. 15, 2013

(54) PROCESS AND APPARATUS TO AUTOMATICALLY REFILL EVAPORATION APPARATUS

(75) Inventor: Herbert J. Hedberg, N. Attleboro, MA (US)

(73) Assignee: Harvard Bioscience, Inc., Holliston, MA (US)

( * ) Notice: Subject to any disclaimer, the term of this patent is extended or adjusted under 35 U.S.C. 154(b) by 616 days.

(21) Appl. No.: 12/824,644

(22) Filed: Jun. 28, 2010

(65) Prior Publication Data

US 2010/0331162 A1 Dec. 30, 2010

Related U.S. Application Data

(60) Provisional application No. 61/220,739, filed on Jun. 26, 2009.

(51) Int. Cl.
*B04B 11/04* (2006.01)
(52) U.S. Cl.
USPC ......... 494/37; 494/6; 494/10; 494/17; 34/312
(58) Field of Classification Search
USPC ............ 34/58, 312–328; 210/198.2; 494/5, 6, 494/10, 16–18, 37–39
See application file for complete search history.

(56) References Cited

U.S. PATENT DOCUMENTS

| | | | |
|---|---|---|---|
| 6,576,137 B1 * | 6/2003 | Ma | 210/657 |
| 2002/0132354 A1 * | 9/2002 | Downs et al. | 422/101 |
| 2008/0164194 A1 | 7/2008 | Hedberg | |
| 2009/0165326 A1 | 7/2009 | Hedberg et al. | |

OTHER PUBLICATIONS

Hedberg, Herbert J. "Process and Apparatus to Automatically Refill Evaporation Apparatus", U.S. Appl. No. 61/220,739, filed Jun. 26, 2009, 15 pages.

* cited by examiner

*Primary Examiner* — Walter D Griffin
*Assistant Examiner* — Timothy Cleveland
(74) *Attorney, Agent, or Firm* — Cesari and McKenna, LLP (57) ABSTRACT

A fraction collector, sample drier that automatically re-fills sample contains is described. Profiles of RPM and/or back EMF decays as a rotating but unpowered rotor comes to a stop are generated. The profiles may be generated for rotors with full, partially filled and empty sample containers. During a drying operation as the non-volatile samples are collected by evaporating the liquids more sample may be loaded while the rotor is spinning. The operation is to unpower the mechanism and measure the decay profile of PPM and/or EMF over time. A threshold may be set so that the lighter rotor will stop more quickly, and if the threshold is crossed the mechanism will load more sample into the containers.

7 Claims, 8 Drawing Sheets

PROCESS AND APPARATUS TO AUTOMATICALLY REFILL EVAPORATION APPARATUS

CROSS-REFERENCE TO RELATED APPLICATIONS

The present application claims the benefit of U.S. Provisional Patent Application Ser. No. 61/220,739, which was filed on Jun. 26, 2009 by Herbert J. Hedberg for a PROCESS AND APPARATUS TO AUTOMATICALLY REFILL EVAPORATION APPARATUS, and which application is hereby incorporated herein by reference.

The present application is closely related to an earlier U.S. patent application Ser. No. 11/901,817, filed Sep. 19, 2007, and that is of common ownership and inventorship with the present application. This earlier patent application is entitled CENTRIFUGAL FRACTION COLLECTOR SYSTEM AND METHOD, which is referred to below as ref. 1, and is incorporated herein by reference.

BACKGROUND OF THE INVENTION

1. Field of the Invention

The present disclosure is related to fraction collection and, more particularly, to automatic re-filling of samples in test tubes or wells that are being dried.

2. Background Information

There are purification processes out that generate liters of fraction liquid which needs to be dried down. This may be accomplished by running a feed tube into a rotary vacuum concentrator and have a technician periodically operate a valve to replenish the liquid in the drying flask as it evaporates away.

The above referenced earlier patent application discussed a rotary fraction collector including a centrifugal fan that dried samples in test tubes. The rotary fraction collector spins a rotor of test tubes, held at an angle, such that sample material, anywhere within a container tube, will be concentrated at the closed end of the tube due to the centrifugal force generated by the spinning rotor (see FIG. 1, item 6). The sample in the tubes may be manually replenished, as indicated just above, when dry.

SUMMARY OF THE INVENTION

The present application realizes that it would be advantageous to replenish the sample fraction liquid tin the drying containers (vials or test tubes or other such containers) while they are spinning in the rotor An embodiment of the present invention uses Hall effect/magnet sensors to measure current dispenser position and to measure rotor RPM. An embedded microprocessor system has on/off control of the rotor motor, and the microprocessor has access to the output of the Hall effect sensors. The system may, at some prescribed timing cycle, power down the rotor, measure the Hall effect signals and generate and store the profile of the rate at which the rotor RPM decays. Or in another embodiment, the micro-processor system may have an analog to digital converter (ADC) where the back EMF (electro-motive force) from an unpowered but rotating motor may be measured and RPM decay profile generated and stored. The decay profiles of an unpowered rotor may be generated for full sample containers, empty sample containers, and various other amounts of liquid remaining in the sample containers. A reasonably continuous decay profile may be generated for any size containers in a rotor.

The more liquid to be dried in the sample containers, the heavier the spinning rotor, and the conservation of angular momentum will keep the rotor spinning. However if some quantity of liquid was lessened due to drying (the amount reduced may be as much as two liters with an 8×250 mL bottle rotor). The microprocessor may detect the decay profile and compare it to the pre-generated decay profiles to determine if the samples should be replenished. The computer may energize a peristaltic feed pump to replenish the empty spinning sample containers. The output of the feed pump would deliver the liquid through exactly the same flow as the initial samples were loaded into the sample containers.

BRIEF DESCRIPTION OF THE DRAWINGS

The invention description below refers to the accompanying drawings, of which.

DETAILED DESCRIPTION OF AN ILLUSTRATIVE EMBODIMENT

The present disclosure is illustrated by the following detailed description, but this invention is not limited to the details of construction and the arrangement of components set forth below. One embodiment does not limit the attached claims. Moreover, the is attached claims are to be read broadly.

Although specific features are shown herein in some drawings and not in others, this is for convenience only as each feature may be combined with any of the other features in accordance with the disclosure. Words "including," "comprising," "having," and "with" as used herein are to be interpreted broadly and comprehensively and are not limited to any physical interconnection.

The above ref. 1 patent application, which is incorporated herein by reference, describes a detailed mechanism that loads samples to be dried into sample container, in this case test tubes. The following is an edited version of ref. 1 that summarizes the contents of ref. 1. The present invention does not rest on the specifics of the mechanism, and the general descriptions of the functions herein will allow one skilled in the art to practice the invention; however, further detail may be found in ref. 1.

Figure 1:
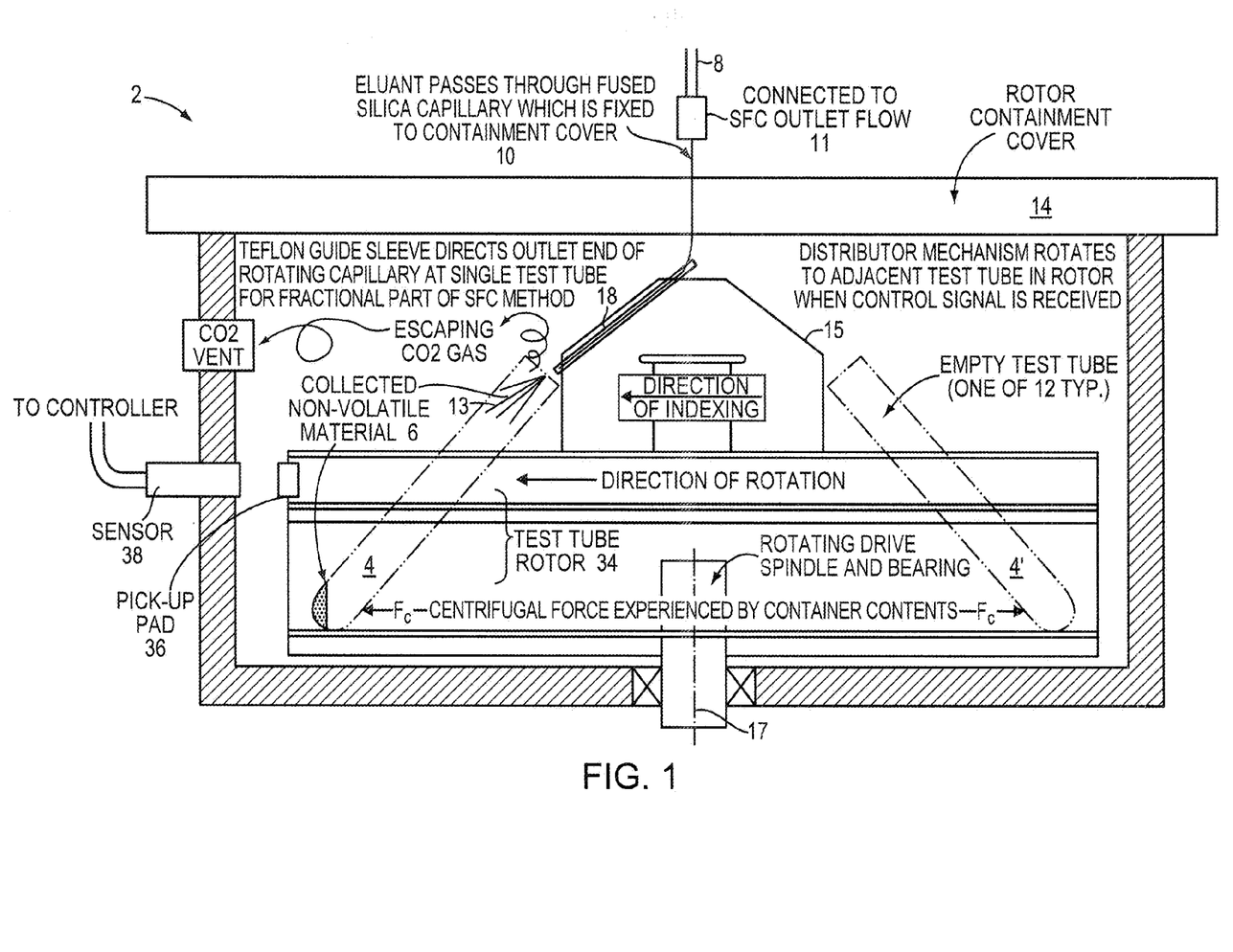
FIG. 1 is a diagram of an embodiment of the present disclosure.

FIG. 1 is of a rotary fraction collector 2 spins a circular rotor 34 of test tubes 4, held at an angle, such that sample material 6 captured anywhere within a container tube will be concentrated at the closed end of the tube due to the centrifugal force generated by the spinning rotor.

Sample material 6 typically including liquid $CO_2$, (typical in super critical chromatography, SFC) is directed into the opening of the test tube 4 from the outlet of a small bore capillary tube 10 (typically 100u ID fused silica with polyamide coating to provide strength). A fluid connection 11 is made between an outlet tube 8 (typically 0.020 inch ID stainless steel) and the inlet end 12 of the fused silica capillary 10. The small ID of the capillary creates a large restriction to flow relative to the larger tube 8. This causes the pressure in the tube 8 to remain high regardless of flow rate and the $CO_2$ to remain in the liquid state.

A pick-up pad 36 is attached to the rotor 34 and rotates with the rotor. The pad may be positioned where a particular collection tube 4 is positioned to receive a sample. That is the capillary tube 10 is at the opening of the containment tube 4. This allows the controller (not shown) to measure and control the RPM of the rotor and, at the same time is know which containment tube is ready to receive sample. The controller may cause a pulse of air, described later, that indexes the capillary tube 10 to a different containment tube. The sensor 38 generates a signal to the controller when the pad passes by. The sensor may be a Hall device, and optical device or other such devices known to those skilled in the art. There may be a pad for each containment tube so that the sensor may pick-up the location of each containment tube.

As the $CO_2$ liquid enters the capillary tubing, the pressure decreases in proportion to the length of the capillary. When the $CO_2$ eluant exits 13 the open end of the capillary inside the rotary fraction collector 2, it is at atmospheric pressure. Therefore, because the pressure drops from 100 or 200 atmospheres tube 8 to 1 atmosphere at the capillary outlet, the $CO_2$ transitions from a liquid to a gas during its passage through the capillary tubing.

The fluid connection 11 delivers a liquid or gas flow to collection tubes 4, 4' inserted in a centrifuge-type rotor forms a rotating liquid-tight joint between the underside of the rotor containment cover 14 and the top of the distributor mechanism 15. The distributor mechanism 15 rotates with the rotor 34 as the rotor. The synchronization of the distributor mechanism 15 and the rotor 34 allows the distributor mechanism to hold the capillary 10 outlet directly opposite the open end of a single test tube 4.

The rotating liquid-tight joint allows the capillary tube 10 to pass through and be fixed to the containment cover 14 in line with the axis 17 of the rotor spindle. The capillary tube 10 is threaded into a hollow Teflon guide sleeve 18 fixed to the top of the distributor mechanism 15. The capillary tube's length is determined such that, when the cover 14 is closed on a rotor full of test tubes, the outlet end of the capillary protrudes slightly into the open end of any given tube.

Figure 2:
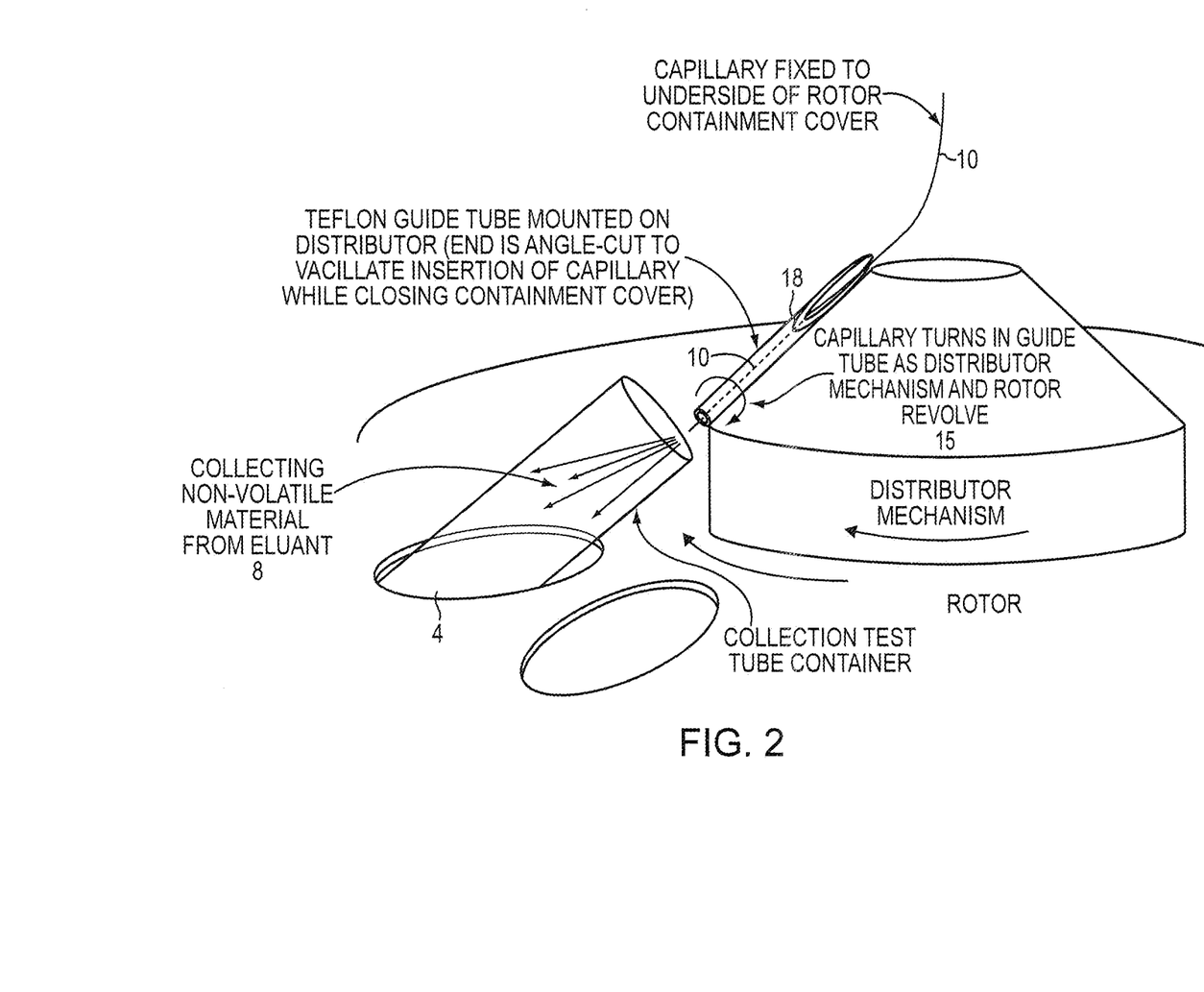
FIG. 2 is an illustration of the capillary, containment tube and sleeve arrangement.

With this configuration, the fused silica capillary 10 rotates within the guide sleeve 18 as the rotor and distributor mechanism rotate together on the rotor drive spindle. Because of the polyamide-coated fused silica capillary's high strength and low tendency to fatigue in a rotational-bending situation, capillaries tested in this mode are able to endure hundreds of thousands of rotations without failure. FIG. 2 illustrates how the guide sleeve 18 simultaneously directs the capillary tube 10 outlet and allows it to turn is within the sleeve 18 as the distributor mechanism turns with the rotor.

The guide sleeve 18 may be of other materials such as certain technical polymers like PEEK, virgin Teflon, and modified such as ETFE (Tefzel). These plastics should have solvent resistance and the ability to survive the cooling effect associated with the expansion of the $CO_2$.

The rotor must spin to generate the centrifugal force to retain the non-volatile eluant components in the containment tubes 4. In addition the weight of the distribution around the rotor must be balance so that fractions can not be collected in adjacent containment tubes 4. Thus the rotary actuator that indexes the capillary tube 10 outlet to the next containment tube to receive sample will advance the capillary tube 10 outlet across several unused tubes to a point about opposite the previously collected tube. By this technique, the weight will be distributed more equally about the circumference of the spinning rotor, thus preventing significant vibration.

Table 1 shows the sequence of collection tube use if the rotor 34 contains 12 equally-spaced tubes and the rotary actuator advances 150° for each fraction.

TABLE 1

Pattern of fraction collection in rotor with 12 collection tubes

| Fraction | Total Degrees | Tube Degrees | Tube Location |
|---|---|---|---|
| 1 | 0 | 0 | 1 |
| 2 | 150 | 150 | 6 |
| 3 | 300 | 300 | 11 |
| 4 | 450 | 90 | 4 |
| 5 | 600 | 240 | 9 |
| 6 | 750 | 30 | 2 |
| 7 | 900 | 180 | 7 |
| 8 | 1050 | 330 | 12 |
| 9 | 1200 | 120 | 5 |
| 10 | 1350 | 270 | 10 |
| 11 | 1500 | 60 | 3 |
| 12 | 1650 | 210 | 8 |
| 13 | 1800 | 0 | 1 |

The design of any components mounted to the spinning rotor must also have their mass fairly evenly distributed about the rotational axis 17.

Distributor Mechanism

Figure 3:
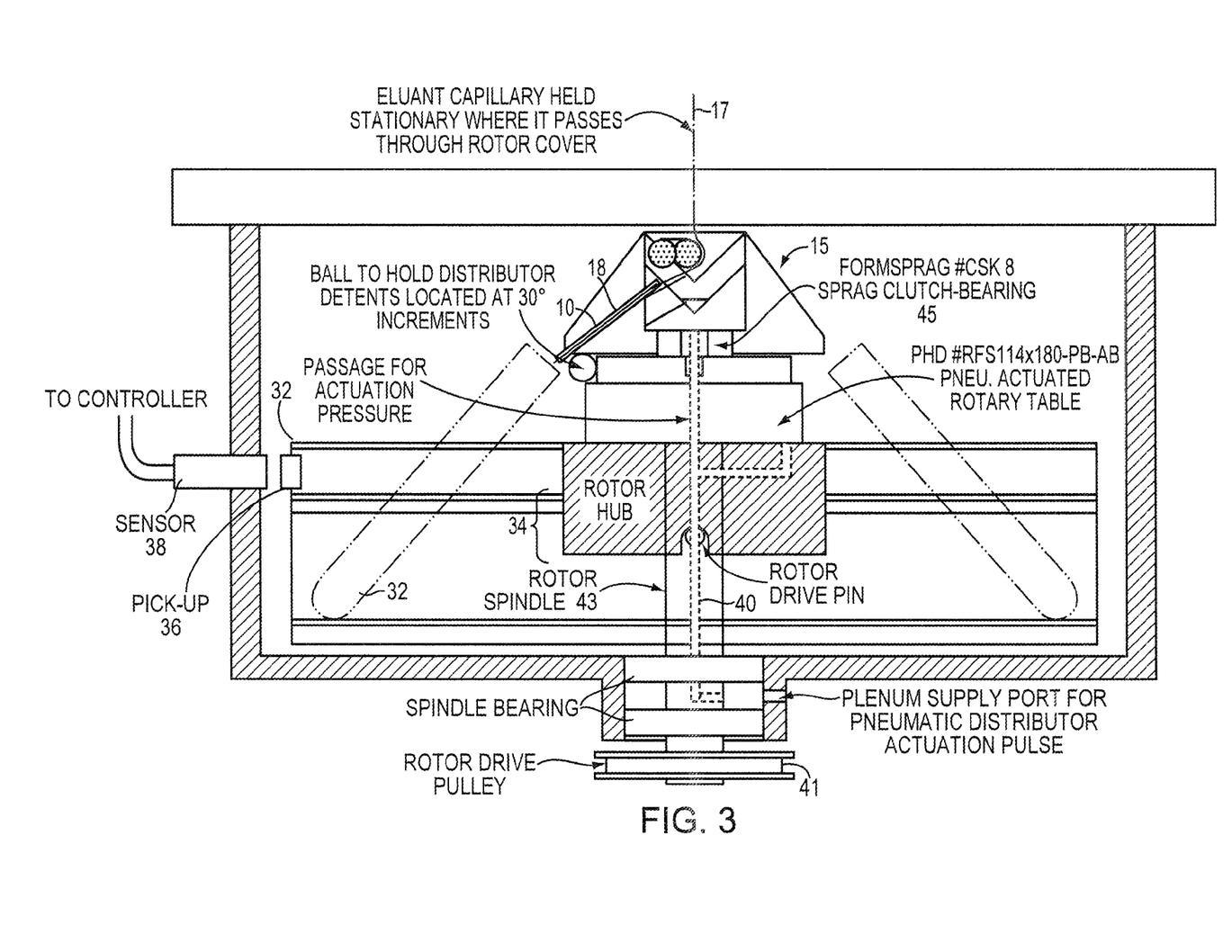
FIG. 3 is an illustration of an embodiment of the present disclosure.

FIG. 3 illustrates the distributor mechanism 15 in more detail, it directs the sample flow to a specific containment tube 4 of the rotor 34 while the rotor is spinning at 1,000 RPM or more. The distributor mechanism 15 responds to a control signal from a controller to relocate the capillary tube 10 outlet from a collection tube to the next among the circular array of tubes 4, 4' inserted into the rotor 34.

When the controller issues a signal to index to the next collection tube, a rotary actuator turns the distributor assembly relative to the rotor to reposition the capillary tube 10 outlet to the opening of an empty tube in the sequence of Table 1. The actuator responds to a pressurized pulse of air delivered through the center of the rotating drive spindle indexing the distributor mechanism 15 while the rotor and distributor mechanism continue to spin at full speed of 1,000 RPM or more.

By periodically sending control signals to the actuator to move the capillary tube 10 output relative to the rotor 34, the non-volatile materials entrained within the eluant flow is distributed to collection tube containers 4 in the rotor 34.

The indexing signal from the controller to the distributor mechanism 15 may communicate across rotating contacts, e.g., a slip ring commutator. Care must be taken when flammable solvents, such as methanol, are used.

Other approaches to indexing the distributor mechanism 15 may include an RF wireless signal or an optical signal.

The controller may have a clock that with the sensor 38 signal allows the controller to measure the RPM. The controller than could control the RPM by the signals sent to the rotor motor that drives the pulleys 41 of FIG. 3.

FIG. 3 shows a preferable implementation which utilizes a pneumatic pulse of moderate pressure air (20 to 50 psi) to index the distributor mechanism. The distributor mechanism receives the air pressure pulse through the hollow center 40 of the rotor spindle 43 where the opposite end turns within a sealed plenum, which is pressurized when the index operation is to occur.

In Table 1, the rotational steps traverse 150°, not the standard 180°. Adjustment is screws (not shown) may be provided which limit the travel of the pneumatic pistons within the mechanism. By making the necessary adjustments, a repeatable 150° actuation cycle can be obtained from the table.

A sprag overrunning clutch 45 may be installed on the rotating table of the actuator. Since the inner race of the clutch is fixed to the table and the outer race is pressed into the bottom of the distributor, the table is only able to drive the distributor in one direction. This allows the actuator table to index the distributor through 150° when the pressure pulse is received, but then allows the table to return to its starting position without moving the distributor further. An array of detents spaced at 30° increments provides re-qualification of the distributor alignment to each collection tube despite slight inconsistencies in the table motion.

Figure 4:
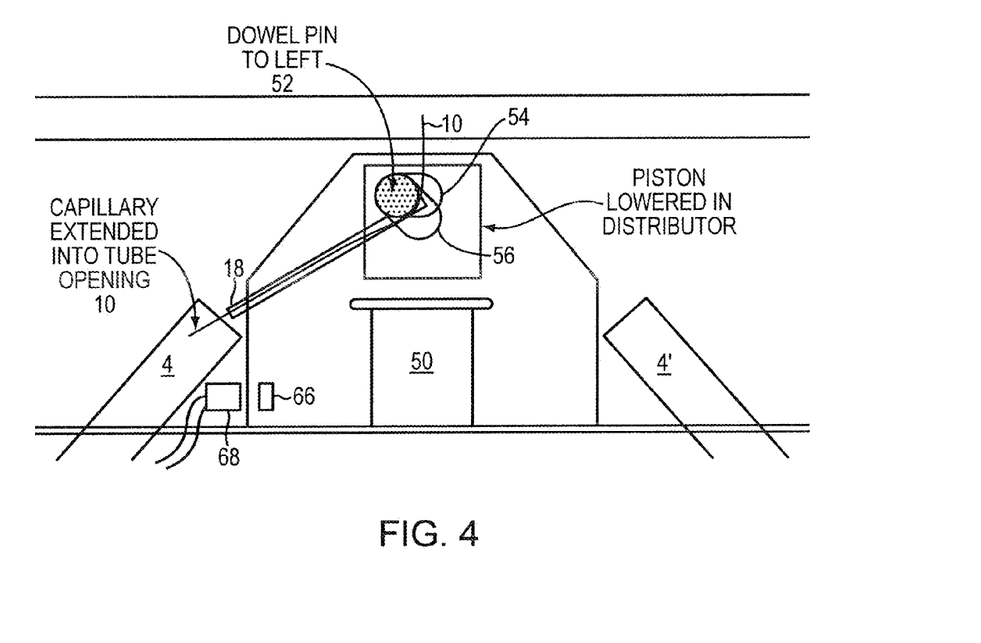
FIGS. 4 and 5 are detailed illustrations of the retraction/insertion of the capillary tube.
Figure 5:
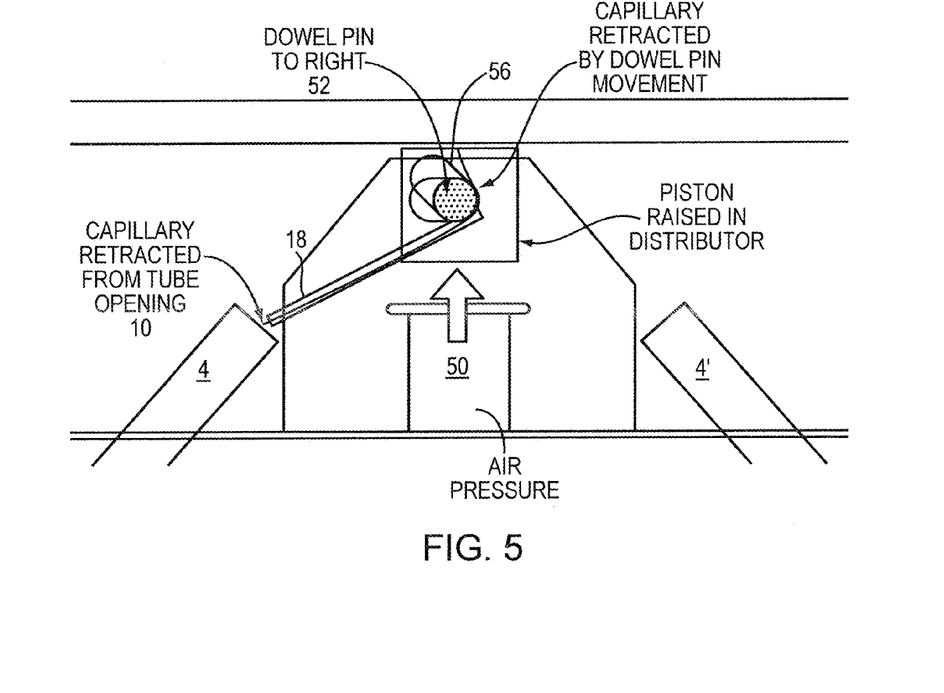

An air passage 40 through the center shaft of the actuator table provides air pressure path 40 that will index the capillary tube 10 retraction mechanism, FIGS. 4 and 5, each time a new containment tube 4 is to be aligned with the capillary tube 10 outlet. FIG. 4 shows a movable piston that acts upon a dowel pin 52 to cause a horizontal displacement 54 in an angled slot 56. Because the eluant capillary bends around the dowel pin, when the pin is pushed closer to the rotor axis, the capillary is retracted from the opening of the collection tube 10; see FIG. 5. When the pressure pulse is removed, the piston retracts to its rest position, FIG. 4, the dowel pin slides away from the axis, and the capillary can extend into the opening of the new collection tube.

The retract moves the capillary tube 10 outlet ¼ inch before indexing to the next tube. The capillary tube 10 outlet then extending the capillary ¼ inch into the new containment tube. The air pulse that indexes to the next containment tube also acts to retract the capillary tube. The mechanisms are arranges so that the capillary tube 10 is retracted before the next containment tube indexing occurs.

FIG. 4 illustrates how a piston installed in the top of the distributor housing is fabricated with an angled slot through which a dowel pin is inserted. When the rotor containment cover is closed, the capillary is directed into the guide tube 18 such that it curves under the dowel pin on its path to the collection tube opening. On the distributor mechanism a pickup pad 66 and sensor 68 may be placed some where on the distributor is mechanism 15 so that the containment tube position of the capillary tube 10 outlet is sensed and sent to the controller.

FIG. 5 illustrates the piston 50 inside the distributor mechanism 15 that is raised by the air pressure pulse used to index (multiple times) to the next collection tube 4. As the piston 50 rises, the angled slot 56 slides the dowel pin 52 to the extreme right side. This movement causes the dowel pin to contact the capillary tube 10 outlet and displace it ¼ inch to the right, effectively retracting its outlet end ¼ inch from the collection tube opening.

This motion occurs at the beginning of the indexing event so that when the distributor mechanism rotates to the next containment tube 4 the outlet end of the capillary tube 10 will not contact the containment tubes. When the index motion is completed and the air pressure is removed, the piston falls back to its lowered position, the dowel pin slides to the left, and the capillary extends into the new collection tube. This motion occurs while the rotor and distributor mechanism are spinning at more than 1,000 RPM.

Figure 6:
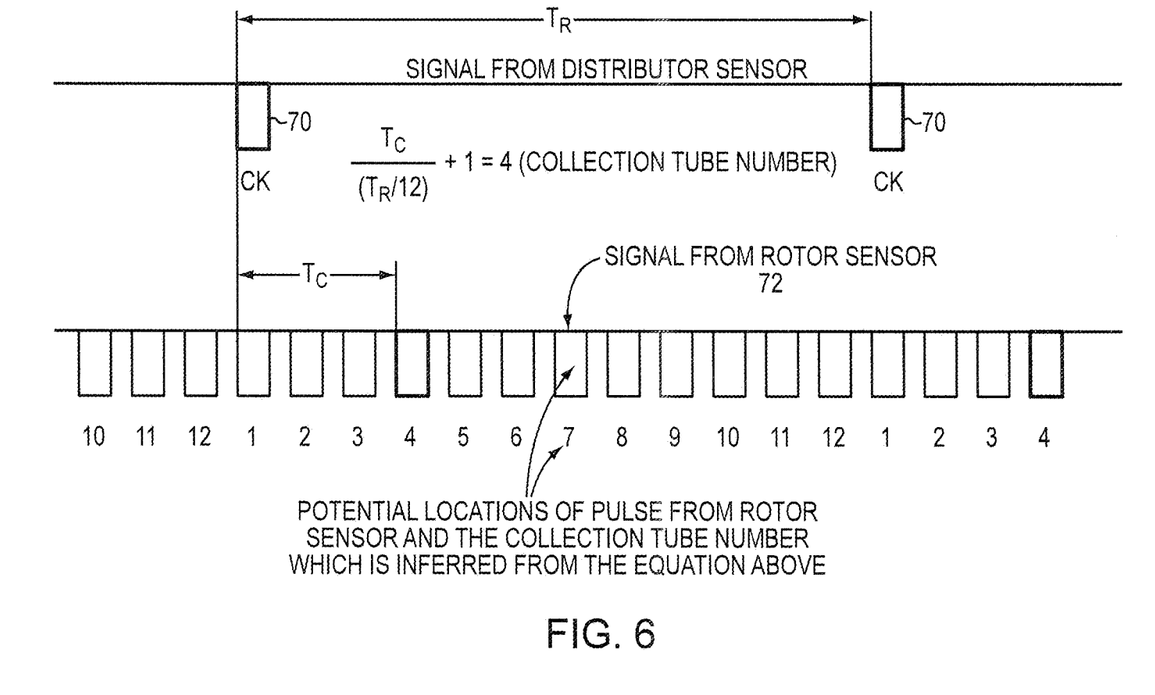
FIG. 6 is a timing diagram showing the clocks.

It may be desirable to confirm into which collection tube 4 the eluant is flowing at any given time. FIG. 6 illustrates how the pulse from the distributor sensor 68 and the pulse from the rotor sensor 38 might appear. The relationship between the two pulses is given by the formula which is valid for a rotor containing 12 collection test tubes. For other rotor configurations, the distributor rotation time period must be divided by the actual number of collection tubes which are equally spaced around the rotor.

The distributor sensor 68 generates a single narrow pulse every revolution of the distributor by magnetic (Hall effect sensor) or optical (retro-reflective tape) means. As before, electrical contacts within the rotor containment environment must be avoided because of the potential for spark ignition of flammable vapors. The detectable element fixed to the distributor, whether tape or magnet, may be located anywhere. The second detection element must be located on the rotor for every containment tube location (12) such that when the eluant is being collected in the first tube, the two pulses occur at the same time.

The signal 70 from the distributor sensor is used to determine the time period of a revolution and secondly to establish a reference point from which the time to the rotor pulse is measured. The rotor pulses 72 occurs a period of time after the distributor pulse, the magnitude of which is dependent upon which tube is currently collecting the eluant. The detection and interpretation of these signals is by the controller. A front panel display would indicate the container into which eluant was currently being collected. A serial communications may link or BCD parallel protocol could keep the controller aware of the fraction number currently being collected.

Figure 7:
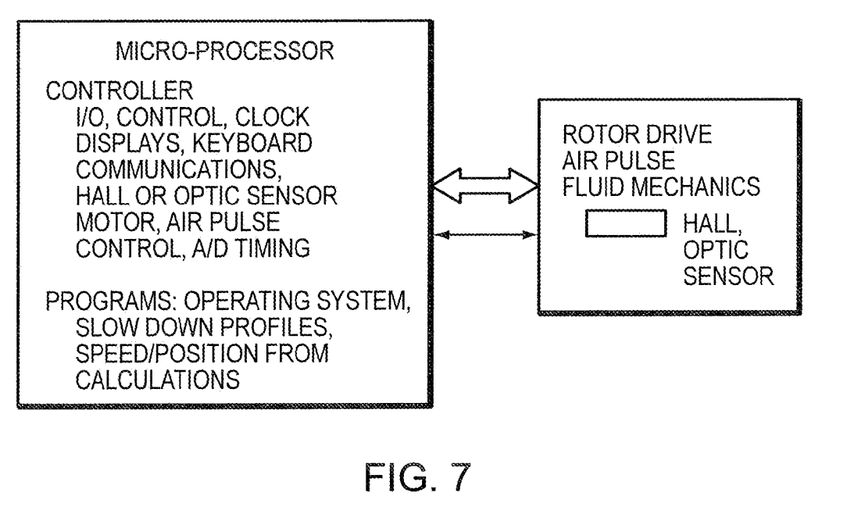
FIG. 7 is a block diagram of the system computer controller.

FIG. 7 illustrates a controller having a micro-processor system. One embodiment of the present disclosure includes a processor system with memory containing an operating system and applications; I/O controllers (display, keyboards, clocks, communications, sensor signal in ports, motor and air pulse controllers, etc.). In particular a motor controller hardware and software applications. The motor controller will drive the motor that rotates the centrifugal mechanism that holds the vials of sample and the air pulse to increment the distributor mechanism.

Hall/magnet devices are mechanically arranged to indicate the position of the containers and the distributor location so that they can be filled. The position devices, that may be optical, mechanical or of embodiments of any of the various commonly found devices, when combined with timing measurements may be used to determine rotor speeds, RPMs. The timing clocks may be found in the micro-processor system.

Figure 8:
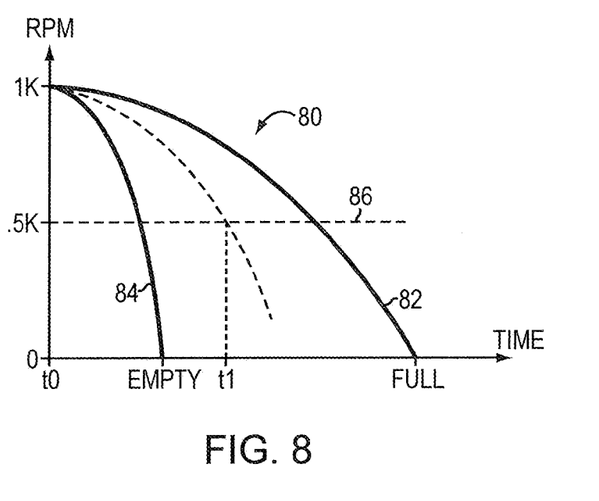
FIG. 8 is a chart showing decay profiles.

FIG. 8 illustrates the RPM of a rotor 34 that is unpowered at T0. Time is measured on the x-axis and the profiles 80 show the time before the rotor stops rotating. A full rotor 82 stays rotating longer than an empty rotor 84. A threshold 86 may be set that when crossed the containment tubes in the rotor may be re-filled. In this case if the RPM of the rotor is less than 0.5K rotation per minute before the time T1, the containment tubes may be refilled. In this operation the threshold may be set where the operator desires and the threshold may be set at a time, wherein the RPM is measured to determine if re-filling is needed. The delay of the rotor may be accomplished at regular intervals as the application may dictate.

As an alternative the back electromotive force (EMF) of the unpowered rotating rotor 34 may be measured as an indicator of the speed of the rotor 34 as it comes to a stop. The profile will be similar to that shown in FIG. 8 where EMF replaces RPM. A threshold may be set and the operation of re-filling will occur just as described above.

Figure 9:
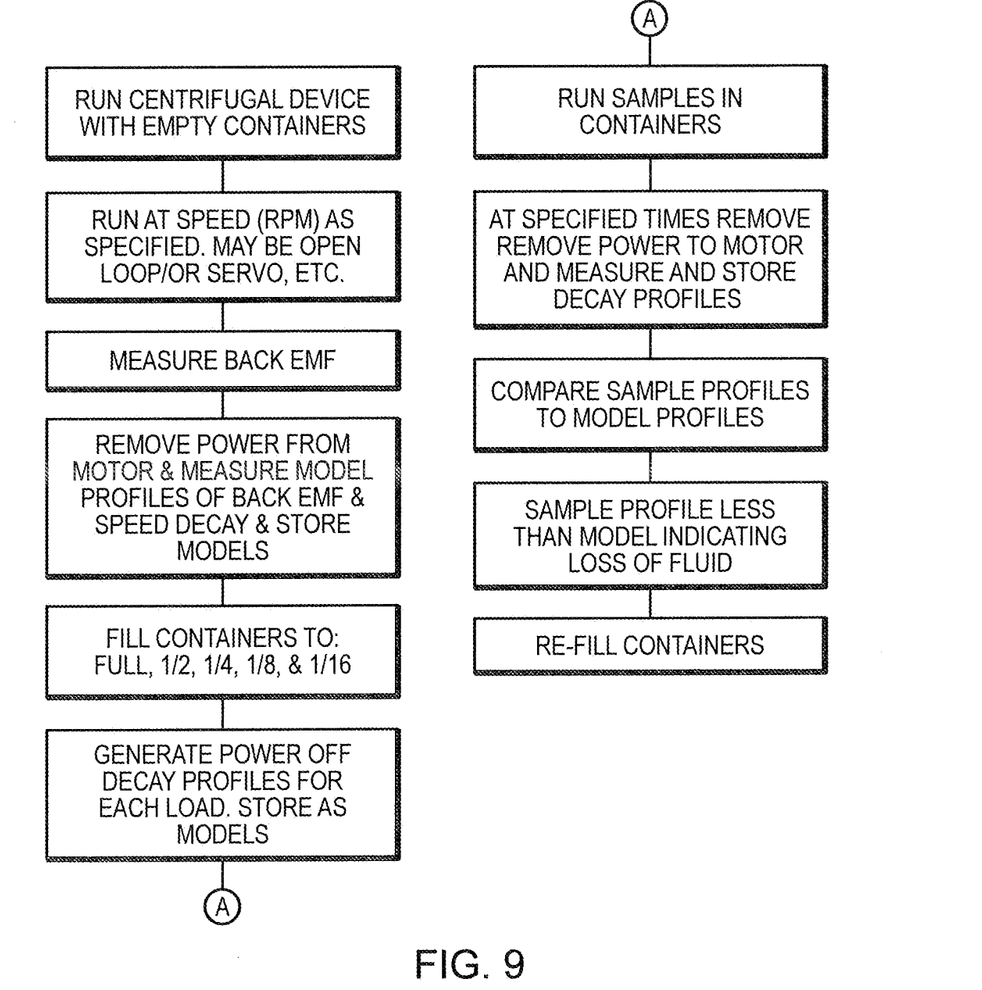
FIG. 9 is a flow chart showing the operation of an embodiment of the present disclosure.

FIG. 9 illustrates one set of processes that may be used to detect and re-fill the sample containers. A base-line set of model profiles may be generated by running the centrifugal device with all vials empty. The actual speed may be set by the motor control output from the micro-processor system or it may be "servoed" by feeding back to position devices compared to a time standard. Regardless of the mechanism, the rotation of the vials will achieve some preset rate (1000 RPM, as mentioned above). At that speed the back EMF may, in some embodiments be measured). At the specified time, the power may be removed from the motor and the centrifugal mechanism will slow down and stop. During the slow down the micro-processor system may measure and store in memory the speed decay and the back EMF profiles. These may represent first model profiles.

The containers or vials than may be filled to, for example, the following illustrative levels: full, ½, ¼, ⅛, and 1/16. With each of these loads the model profiles may be run and, together with the first model profiles a set of model profiles may be developed and stored.

Then actual samples may be loaded into the containers and run. When the solvent evaporates, the mass in the containers is diminished. At some specified time (that may depend on the local circumstances) the power may be removed from the motor and the speed and back EMF profiles measured and stored. These profiles may be compared to the model profiles and the loss of solvent in the containers may be calculated. When the loss of mass reaches some threshold, say the containers are less than ⅛ filled, the micro-processor system may fill the vials with more sample containing fluid. This process may be repeated as often as the operators may determine. The set-up of where the threshold is et also will determine how much more sample is needed to re-fill the sample containers. As described above, when the threshold is set to be crossed when the container are less is than ⅛ filled, the system may reload ⅞ of the initial full amount into the containment tubes to bring them back to fully loaded. Other threshold may be set so that other amount may be loaded to re-fill the containment tubes. For example the re-filling may occur when ½ of the original sample amount remains in the containment tubes.

One advantageous consequence is that larger amounts of sample may be collected with very little human intervention.

Note that the mechanisms shown herein illustrate the liquid or fluid systems that will load liquid bearing samples into the vials. The mechanisms that dry or evaporate the solvent from the vials may be the mechanical system described in U.S. patent application Ser. No. 12/038,405, of common ownership with the present application, filed Feb. 27, 2008 and entitled APPARATUS AND METHOD FOR DRYING A SOLID OR LIQUID SAMPLE. The mechanisms of this utility application may physically overlay and co-exist with the mechanism shown in the present application.

What is claimed is:

1. A process for detecting when to automatically re-fill containment tubes housed in a rotor, the process comprising:
    generating slow down decay profiles of the rotor bearing containment tubes, the respective profiles corresponding to the containment tubes having different amounts of sample and being based on speeds of rotation of the rotor over time when power is removed from a motor attached to the rotor;
    setting a threshold for directing the re-filling of the containment tubes based on the profiles, the threshold corresponding to a particular amount of sample in the containment tubes; and
    determining that the containment tubes are ready to be re-filled if the threshold is crossed after power is removed from the motor attached to the rotor.

2. The process of claim 1 wherein generating slow down decay profiles includes:
    generating a first profile corresponding to filled containment tubes by rotating the rotor having filled containment tubes by applying power to the motor attached to the rotor, removing power from the motor, and generating the first decay profile as the rotor slows down;
    generating a second decay profile corresponding to empty containment tubes by rotating the rotor having empty containment tubes by applying power to the motor attached to the rotor, removing power from the motor, and generating the second decay profile as the rotor slows down, and
    generating a third decay profile corresponding to partially filled containment tubes that contain a sample amount that lies between the amounts used for the first and the second profiles by rotating the rotor having partially filled containment tubes by applying power to the motor attached to the rotor, removing power from the motor, and generating the third decay profile as the rotor slows down, and
    selecting as the threshold a back EMF and/or an RPM versus time that corresponds to a point on the third decay profile.

3. The process of claim 2 further comprising:
    determining if the threshold was crossed, and
    if the threshold is not crossed, applying power to the motor so that the rotor resumes its normal RPM, and
    if the threshold is crossed, applying power to the motor so that the rotor resumes its normal RPM and reloading sample into the sample containment tubes.

4. The process of claim 3 wherein the reloading of sample into the sample containment tubes comprises:
    setting up the threshold to be crossed when only a first portion of an original sample amount loaded into the containment tubes remains in the tubes; and
    refilling the containment tubes until the containment tubes are re-filled to a level that corresponds to the original sample amount.

5. The process of claim 1 wherein the refilling of the containment tubes comprises:
    loading into the containment tubes less than an amount that will refill the containment tubes to the level that corresponds to an original sample amount; and
    loading additional increments into the containment tubes, until the containment tubes are refilled to the level that corresponds to the original sample amount.

6. The process of claim 1 wherein the decay profiles are the profiles of back EMF versus time.

7. The process of claim 1 wherein the decay profiles are the profiles of RPM versus time.

* * * * *